United States Patent [19]

Mauro

[11] Patent Number: 5,689,002
[45] Date of Patent: Nov. 18, 1997

[54] PROCESS FOR THE CRYSTALLIZATION FROM WATER OF (S)-N,N'-BIS[2-HYDROXY-1-(HYDROXYMETHYL)ETHYL]-5-[2-HYDROXY-1-OXOPROPYL)AMINO]-2,4,6-TRIIODO-1,3-BENZENDICARBOXAMIDE

[75] Inventor: Marina Mauro, Milan, Italy

[73] Assignee: Bracco International B.V., Amsterdam, Netherlands

[21] Appl. No.: 708,668

[22] Filed: Sep. 5, 1996

[30] Foreign Application Priority Data

Sep. 8, 1995 [IT] Italy ................... RM95A0599
Dec. 19, 1995 [IT] Italy ................... RM95A0831

[51] Int. Cl.[6] .................. C07C 231/22; C07C 231/24
[52] U.S. Cl. .......................... 564/153; 424/9.454
[58] Field of Search .................... 564/153; 424/9.454

[56] References Cited

U.S. PATENT DOCUMENTS 4,001,323  1/1977  Felder et al. .................. 564/153
5,571,941  11/1996 Villa et al. .................... 564/153

*Primary Examiner*—Richard L. Raymond
*Attorney, Agent, or Firm*—Nixon & Vanderhye P.C.

[57] ABSTRACT

This invention refers to a process for the crystallization from water of S-N,N'-bis[2-hydroxy-1(hydroxymethyl)ethyl]-5-[(2-hydroxy-1-oxopropyl)amino]-2,4,6-triiodo-1,3-benzendicarboxamide known as Iopamidol.

According to the process of this invention, a crystalline anhydrous Iopamidol in accordance with pharmacopeia standards can be obtained.

8 Claims, No Drawings

PROCESS FOR THE CRYSTALLIZATION FROM WATER OF (S)-N,N'-BIS[2-HYDROXY-1-(HYDROXYMETHYL)ETHYL]-5-[2-HYDROXY-1-OXOPROPYL)AMINO]-2,4,6-TRIIODO-1,3-BENZENDICARBOXAMIDE

This invention refers to a process for the crystallization from water of S-N,N'-bis[2-hydroxy-1(hydroxymethyl)ethyl]-5-[(2-hydroxy-1-oxopropyl)amino]-2,4,6-triiodo,13-benzendicarboxamide, best known as Iopamidol, which is one of the world top compounds in the field of non-ionic X-ray contrast media. The syntheses of Iopamidol known in literature, for instance the one described in GB 1472050, foresee a final purification at the end of the process, by using ion-exchange resins and successive recrystallization from EtOH, which produces a water-soluble product (2.3 g of product crystallize from a solution of 10 g of Iopamidol in 10 mL of water during some days in a fridge at 4° C.). This good solubility is reported in articles successively published, such as Felder E. et al, Boll. Chim. Farm., 1981, 120, 639, or Felder E., Invest. Radiol., 1984, 19, S164 and the monography on Iopamidol in Analytical Profiles of Drug Substances, vol. 17, 115, together with the scarce solubility in MeOH and the insolubility in $Et_2O$, benzene, chloroform and EtOH.

Said articles describe the different crystalline forms of Iopamidol, i.e. anhydrous, monohydrated and pentahydrated, each form having a different IR spectrum, X-ray powder diffraction patterns and distinct enthalpimetric and gravimetric thermograms. Said crystals have been obtained with a very slow kinetics from aqueous solutions.

Recently the patent application WO-A-9504031 mentions different solvents (n-BuOH, i-BuOH and/or t-BuOH) from which Iopamidol crystallizes. Moreover, this application describes the attempts to crystallize Iopamidol from water for obtaining a product in accordance with the pharmacopeia standards (for instance that of United States of America (US Pharmacopeia XXII, 712)), but with poor results, due to the low yields and the necessity of removing the crystallization water prolonged heating at temperature higher than 100° C.

We have now surprisingly found out that, and this is an object of the present invention, Iopamidol can be easily crystallized from water with industrially acceptable yields, thus giving a product which meets the pharmacopeia standards.

In fact, according to the process of this invention, a crystalline anhydrous Iopamidol in accordance with pharmacopeia standards can be obtained.

Furthermore, according to the process of the invention, the use of water as crystallization solvent for Iopamidol is particularly important in a responsible and up-to-date environmental policy since it avoids the use of organic solvents.

The process of this invention comprises the following steps:
dissolution of Iopamidol in deionized water by heating;
decolorisation of the solution with active carbon;
vacuum-concentration of the aqueous solution at 60° C.;
addition of crystalline germs of anhydrous Iopamidol for seeding the crystallisation;
crystallization at 60° C.;
filtration of the resulting precipitate;
vacuum-drying of the wet product.

Particularly preferred are the crystallization conditions in which the Iopamidol concentration in water is higher than 78.6% (g/mL of solution), being the solution saturated, in presence of variable amounts of suitable germs of crystallization (1%–5%–10%).

Anhydrous Iopamidol obtained according to the process of this invention does not absorb humidity, while the amorphous product, resulting from the simple concentration to dryness of the aqueous solutions of Iopamidol, immediately absorbs water by solubilisation into the same.

It has been surprisingly found that, and this is another object of the present invention, whenever the product obtained according to the process of this invention contains residual solvents coming from previous synthetic steps, a simple washing of the crystalline solid with a suitable quantity of a linear or branched ($C_1$–$C_4$) alcohol, decreases the contents of said residual solvent to amounts lower than 10 ppm.

The washing is particularly useful for removing, for example, dimethylacetamide, a solvent used in the synthetic way for Iopamidol synthesis disclosed in patent GB 1472050.

Particularly preferred is the use of abs. ethyl alcohol, for its easy availability, its known toxicological profile and its easy industrial disposal.

The following examples are aimed at illustrating the best experimental conditions in order to carry out the process of this invention.

EXAMPLE 1

Crystallization from water of Iopamidol

A solution of 500 kg of Iopamidol in 600 kg of deionized water is decolorised using 5 kg of Carbopuron®. The suspension is filtered and washed with 100 kg of water. The solution is concentrated at approx. 60° C. and at 150 mm Hg up to a volume of 370 L (625 kg) and germinated with 1 kg of anhydrous crystalline germs. The solution crystallizes during 8 h while the temperature is carefully kept at 60° C. Then it is filtered at 60° C. without washing and the aqueous liquors are collected (210 kg). After concentration to dryness (5–30 mm Hg) at 60° C., 350 kg of the desired product are obtained.

Yield: 69.9%

The product physico-chemical characteristics are in accordance with pharmacopeia standards.

EXAMPLE 2

Recovery of Iopamidol from mother liquors obtained according to EXAMPLE 1

The mother liquors deriving from three crystallization on batches of 500 kg of Iopamidol are collected together and diluted with 285 L of deionized water. At 80° C., the solution is decolorised with 5 kg of Carbopuron ® and filtered. The filter is washed with 100 kg of water. At 60° C. and 150 mm Hg the solution is concentrated to give a residue of 333 L, then it is germinated with 1 kg of the product of the previous preparations. The product crystallizes during 8 h and at 60° C. Then it is filtered without washing, 355 kg of wet product are concentrated under vacuum at 60° C., thus giving 316 kg of Iopamidol.

Yield (on dried product): 63%

Yield of crystallization starting from EXAMPLE 1: 90.9%

The product physico-chemical characteristics are in accordance with pharmacopeia standards.

EXAMPLE 3

Purification of crystals obtained according to EXAMPLE 1, when a residue of dimethylacetamide is present.

The crystalline solid obtained after filtration according to the procedure of EXAMPLE 1, having a dimethylacetamide content equal to 50 ppm, is washed with absolute ethyl alcohol 5 times (ratio equal to 12.5% weight of EtOH w/w of Iopamidol) and the resulting solid is dried at 50° C. under vacuum.

The analysis of the resulting product shows a content of dimethylacetamide equal to 16 ppm.

I claim:

1. A process for the crystallization from water of Iopamidol to give said compound in a crystalline anhydrous form and in accordance to the pharmacopeia standards comprising the following steps:

dissolution of Iopamidol in deionized water by heating;
  decolorisation of the solution with active carbon;
  vacuum-concentration of the aqueous solution at 60° C.;
  addition of crystalline germs of anhydrous Iopamidol for seeding the crystallization;
  crystallization at 60° C.;
  filtration of the resulting precipitate;
  vacuum-drying of the wet product.

2. A process according to claim 1, wherein the Iopamidol concentration in the aqueous solution is more than 78.6 (g/mL of solution).

3. A process according to claim 1, wherein the crystalline germs of the anhydrous form of Iopamidol are added in amounts from 1 to 10% of the starting Iopamidol1.

4. A process according to claim 1, wherein the filtered crystalline solid is further washed with a linear or branched ($C_1$–$C_4$) alcohol.

5. A process according to claim 4, wherein said alcohol is ethyl alcohol.

6. The process according to claim 1 wherein said Iopamidol prior to dissolution in water contains residual solvents and after crystallization, the crystals of Iopamidol are washed with a linear or branched $C_1$–$C_4$ alcohol, whereby the content of said solvents is reduced.

7. The process according to claim 6 wherein said solvents include dimethylacetamide.

8. The process according to claim 7 wherein said alcohol is ethyl alcohol.

* * * * *